United States Patent [19]

Meier et al.

[11] Patent Number: 4,623,669

[45] Date of Patent: Nov. 18, 1986

[54] FISCHER-TROPSCH CATALYSTS

[75] Inventors: Paul F. Meier; Filippo Pennella, both of Bartlesville, Okla.

[73] Assignee: Phillips Petroleum Company, Bartlesville, Okla.

[21] Appl. No.: 713,731

[22] Filed: Mar. 20, 1985

[51] Int. Cl.$^4$ ............................................. C07C 1/04
[52] U.S. Cl. .................................... 518/719; 518/715; 518/717; 502/258; 502/260; 502/325
[58] Field of Search ............................... 518/715, 719

[56] References Cited

U.S. PATENT DOCUMENTS

| | | | |
|---|---|---|---|
| 2,234,568 | 3/1941 | Linckh | 518/219 |
| 2,548,801 | 4/1951 | Latta | 518/215 |
| 2,564,985 | 8/1951 | Mayland | 260/449.6 |
| 2,583,254 | 1/1952 | Clark | 260/449.6 |
| 2,593,250 | 4/1952 | Black et al. | 260/449.6 |
| 2,623,058 | 12/1952 | Mattox | 518/215 |
| 2,636,011 | 4/1953 | Clark | 252/411 |
| 2,637,739 | 5/1953 | McGrath | 260/449.6 |
| 2,642,448 | 6/1953 | Mayer et al. | 260/449.6 |
| 2,786,070 | 3/1957 | Rottig | 260/449.6 |
| 3,591,649 | 7/1971 | Kroll et al. | 260/667 |
| 3,988,334 | 10/1976 | Finch et al. | 260/449.6 |
| 4,154,751 | 5/1979 | McVicker et al. | 260/449.6 R |
| 4,340,503 | 7/1982 | Rao et al. | 252/459 |

FOREIGN PATENT DOCUMENTS 596162 12/1947 United Kingdom .

OTHER PUBLICATIONS

Klabunde, K. J., et al, "Solvated Nickel Atoms and Their Free Cluster Formation in Organic Media", *Journal of the American Chemical Society*, 98:4, 1021 (1976).

Klabunde, K. J., et al, "Clustering of Metal Atoms in Organic Media", *Journal of Catalysis*, 54, 254 (1978).

Klabunde, K. J., et al, "Clustering of Metal Atoms in Organic Media", Journal of the American Chemical Society, 103, 3024 (1981).

Klabunde, K. J., et al, "Clustering of Metal Atoms in Organic Media", *Journal of the American Chemical Society*, (1978).

*Primary Examiner*—Howard T. Mars
*Attorney, Agent, or Firm*—Mark A. Montgomery

[57] ABSTRACT

A Fischer-Tropsch catalyst is prepared using a solvated metal atom technique. The thus formed catalyst is active for the conversion of carbon monoxide and hydrogen to hydrocarbons though it contains less than about 5% metal by weight of the catalyst.

12 Claims, No Drawings

FISCHER-TROPSCH CATALYSTS

This invention relates to a process for converting a mixture of carbon monoxide and hydrogen, such as synthesis gas, to hydrocarbons. In particular it relates to a process for converting a mixture of carbon monoxide and hydrogen to higher alkanes. In particular it relates to a catalyst useful for converting a mixture of carbon monoxide and hydrogen to hydrocarbons, particularly higher alkanes. It also relates to a process for preparing a catalyst useful in converting carbon monoxide and hydrogen to hydrocarbons and particularly higher alkanes.

The process for producing hydrocarbons from carbon monoxide and hydrogen in the presence of a catalyst is generally known as the Fischer-Tropsch synthesis. The conventional Fischer-Tropsch synthesis is carried out using a metal of the VIIIth Group of the Periodic System. The most commonly used metals are iron, cobalt, nickel and ruthenium. Other metals or metal oxides can be used as well to promote activity or selectivity. This mixture of metals can be used in bulk form or supported on a high surface area support such as silicon dioxide, aluminum oxide, magnesium oxide, and the like.

Preparation of these catalysts is accomplished through co-precipitating, sintering, or impregnating a support with the metals. For example cobalt, iron or nickel nitrate can be used to impregnate a support such as silica and this nitrate impregnated support is heated or calcined to form the metal oxide. This compound is then reduced by heating the mixture in presence of hydrogen to about 500° C. The thus prepared catalyst is then suitable for use to convert carbon monoxide and hydrogen to hydrocarbons.

The activity of this catalyst is related to the amount of reduced catalyst metal and the dispersion or crystallite sizes of the reduced metal particles. The ability to reduce the metal catalyst is crucial since the zero valent metal is considered the active species in synthesis gas conversion.

In prior catalysts, the metal is generally present in the range from greater than about 5% to about 25% by weight of the support or even greater amounts. Catalysts prepared in this method using smaller than about 5% metal content are fairly inactive for converting carbon monoxide and hydrogen to hydrocarbons.

The object of this invention is to provide a new method of preparing a Fischer-Tropsch catalyst. Another object of this invention is to provide a catalyst with low metal concentration on the support. Another object of this invention is to provide an active catalyst for converting carbon monoxide and hydrogen to hydrocarbons.

SUMMARY OF THE INVENTION

According to the instant invention a catalyst active for the Fischer-Tropsch synthesis is prepared by depositing the metal on the support material using the solvated metal atom technique. This technique involves vaporizing the metals under a vacuum, dispersing the metal in a solvent at low temperatures, melting the solvent and metal in the presence of a support material and vacuum drying off the solvent, leaving the metal and the support. Although these catalyst contain less than about 5% metal by weight on the support, they are active for the synthesis of hydrocarbons from carbon monoxide and hydrogen. These catalysts also have the advantage in that they do not have to be reduced in the presence of hydrogen before use, saving a step in the processing of the catalyst.

DETAILED DESCRIPTION OF THE INVENTION

The metals used in this invention are those that are active for at least partially converting carbon monoxide and hydrogen to hydrocarbons and include the metals of Group VIII of the Periodic Table. Metals particularly suitable under this invention are iron and cobalt.

The metal can be impregnated onto any support material. Typical support materials include silicon dioxide, aluminum oxide, molecular sieve, activated carbon, magnesium oxide, titania and mixtures thereof. Preferably in this invention the support material is silicon dioxide.

The metal is impregnated onto the support material through a solvated metal atom technique. This technique is described in "Clustering of Metal Atoms in Organic Media", Klabunde, K. J., Davis, S. C., Hattori, H., and Tanaka, Y., *Journal of Catalysis,* 54, 254 (1978); "Solvated Nickel Atoms and Their Free Cluster Formation in Organic Media", Klabunde, K. J., Efner, H. F., Murdock, T. O., and Ropple, R., *Journal of the American Chemical Society,* 98, 1021 (1976); and "Clustering of Metal Atoms in Organic Media", Klabunde, K. J., Ralston, D., Zoellner, R., Hattori, H., and Tanaka, Y., *Journal of Catalysis,* 55, 213 (1978); all of the above hereby incorporated by reference.

Any amount of metal can be deposited onto the support material. An advantage of this invention is that only small amounts need to be used to have an active catalyst. Generally the amount of metal present will range from a small effective amount to about 5% by weight based on the weight of the support. Preferably about 2 to about 5 weight percent, based on the weight of the support, will be present.

In the solvated metal atom technique, metals are vaporized in the presence of a solvent by heating the metals under a vacuum, dispersing them into the solvent medium. The vaporous solvent/metal mixture is then cooled to very low temperatures, such as the temperature of liquid nitrogen ($-196°$ C.). The resulting cocondensed solvent/metal solid mixture is then slowly warmed and melted in the presence of the support material. After melting, the mixture is vigorously stirred and a metal-solvent/support slurry is obtained.

The mixture is then vacuum dried at about $10^{-3}$ Torr to remove the solvent. The resulting solid is air sensitive and is handled under an inert atmosphere. This catalyst is then active for synthesis gas conversion. No pretreatment or reduction step is necessary for this catalyst, and as shown in the examples, such a step can be harmful.

The compounds useful for the organic solvent medium includes any of several well known solvents. Such solvents include pentane, hexane, toluene, tetrahydrofuran and dioxane and mixtures thereof. In the preferred embodiment of the invention the organic solvent medium is toluene.

The catalyst can be used in any synthesis gas ($H_2$ plus CO) conversion. It is particularly useful in the Fischer-Tropsch reaction, of which a typical process is described in U.S. Pat. No. 2,786,070 hereby incorporated by reference. The general conditions of the process include a temperature ranging from about 150° C. to about 450° C., a pressure ranging from about atmospheric (1 atm) to about 1000 atmospheres, a hydrogen to carbon monoxide mol ratio of between about 0.2 and about 6, and a space velocity of about 500 to about 50,000 volume feed gas/volume catalyst/hour. The preferred conditions of the process are a temperature ranging from about 150° C. to about 350° C., a pressure ranging from about 1 to about 30 atmospheres, a $H_2/CO$ mol ratio of about 1 to about 2.5, and a space velocity of about 500 to about 2000 vol/vol/hr.

The following examples provide more details to the operation of this invention.

EXAMPLE I

In this example, the experimental procedure used to test the performance of the catalysts of Examples II, III, and IV in the conversion of synthesis gas (a mixture of $H_2$ and CO) is described.

The catalytic tests were carried out in a fixed-bed, single-pass flow-through system with a 1" ss reactor tube charged with 10 mls of the catalyst. The space above the catalyst was filled with quartz chips, which acted as a preheater. Normally, the experiments were run for about 28 hours. Liquid and solid hydrocarbons and aqueous products were condensed out at −20° C. and collected at the end of the test. The hydrocarbon products were analyzed on an HP5710A chromatograph with an OV-101 column while aqueous products were analyzed on an HP5750 chromatograph with a Poropak Q column. Gaseous products were analyzed periodically during the test on a Carle Multicolumn chromatograph (Refinery Gas GC 111H, Series S).

EXAMPLE II

The invention catalyst was prepared by vaporizing 1.44 g of cobalt metal at 1400° C. with toluene in the presence of 20 g of Ketjen silicon dioxide. Analysis of the final catalyst indicated the invention catalyst contained 4.8 wt. % cobalt.

A control catalyst was prepared by combining cobalt nitrate hexahydrate and Ketjen silicon dioxide using an incipient wetness technique. In this preparation, 7.1 g of the cobalt compound were added to 27.7 mls of water, and the solution was slurried with 28.6 g of Ketjen silicon dioxide. The catalyst was dried 17 hours at 110° C. and then calcined one hour at 350° C. The control catalyst contained 4.5 wt. % cobalt.

Each of these catalysts was tested at about 230° C., about 6 bars, a $H_2$:CO ratio of about 2, and a space velocity of about 720 GHSV. The control catalyst was pretreated for 17 hours with 80 mls/min hydrogen at 500° C. The invention catalyst received no pretreatment. The following table summarized the experimental results.

TABLE 1

| Results | Invention Catalyst | Control Catalyst |
|---|---|---|
| CO conversion to hydrocarbons | 31% | Inactive |
| Distribution, carbon mole % | | |
| CH$_4$ | 22% | Traces |
| C$_2$-C$_4$ (total) | 20% | |
| C$_2$-C$_4$ (olefins) | 6% | |
| C$_5$+ Hydrocarbons | 55% | |
| Alcohols | 3% | |

Data in Table I shows that the cobalt-containing invention catalyst was active at low metal loading (<5 weight-% Co) while the control catalyst prepared by a conventional method was inactive at a low metal loading of <5 weight-%.

EXAMPLE III

The invention catalyst was prepared by vaporizing 0.96 g of iron metal at 1400° C. with toluene in the presence of 20 g of Ketjen silicon dioxide. Analysis of the final catalyst indicated the catalyst contained 3.3% iron.

A control catalyst was prepared by combining iron nitrate nonahydrate and Ketjen silicon dioxide using an incipient wetness technique. In this preparation, 7.2 g of the iron compound were added to 27.9 mls of water and slurried with 29.0 g Ketjen silicon dioxide. The catalyst was dried 17 hours at 110° C. and then calcined one hour at 350° C. and three hours at 500° C. This control catalyst contained 3.3 wt. % iron.

Each of these catalysts was tested at about 320° C., about 11 bars, a $H_2$:CO ratio of about 1, and a space velocity of about 720 GHSV. The control catalyst was pretreated 17 hours with 80 ml/minute hydrogen at 500° C. The invention catalyst received no pretreatment. The following table summarizes the results.

TABLE II

| Results | Invention Catalyst | Control Catalyst |
|---|---|---|
| CO conversion to hydrocarbons | 24% | Inactive |
| Distribution, carbon mole % | | |
| CH$_4$ | 34% | Traces |
| C$_2$-C$_4$ (total) | 54% | |
| C$_2$-C$_4$ (olefins) | 30% | |
| C$_5$+ Hydrocarbons | 11% | |
| Alcohols | 1% | |

Data in Table II shows that the Fe-containing invention catalyst was active at low metal loading (3-4 weight-% Fe) while the control catalyst prepared by a conventional method was inactive at a low metal loading of 3-4 weight-%.

EXAMPLE IV

The 4.8 wt. % Co/SiO$_2$ invention catalyst of Example II was heated to 350° C. in the presence of flowing nitrogen gas. Then, air was gradually added to the gas stream, never allowing the catalyst temperature to exceed 365° C. After the catalyst was oxidized as indicated by no further rise in temperature, pure air was added and the catalyst temperature was raised to 500° C. This temperature was maintained for four hours. Next, the air was flushed out with nitrogen gas, and hydrogen was gradually added to the gas stream until a pure hydrogen feed was obtained. The catalyst was reduced with 80 ml/minute of hydrogen at 500° C. for 17 hours.

An analogous treatment was done on the 3.3 wt. % Fe/SiO$_2$ invention catalyst of Example III. In this manner, the two invention catalysts were calcined and reduced with hydrogen in a similar manner to the control catalysts. Next, the two catalysts were tested for Fischer-Tropsch activity. As before, the cobalt catalyst was tested at 230° C., 6 bars, a $H_2$:CO ratio of 2, and a space velocity of 720 GHSV and the iron catalyst at 320° C., 11 bars, a $H_2$:CO ratio of 1, and a space velocity of 720 GHSV.

The following table summarizes the results.

TABLE III

| Results | Co/SiO$_2$ Catalyst-calcined and reduced | Fe/SiO$_2$ Catalyst-calcined and reduced |
| --- | --- | --- |
| CO conversion to hydrocarbons | 3% | 1% |
| Distribution, carbon mole % | | |
| CH$_4$ | 27% | 27% |
| C$_2$-C$_4$ (total) | 22% | 73% |
| C$_2$-C$_4$ (olefins) | 6% | 56% |
| C$_5$+ Hydrocarbons | 51% | 0% |
| Alcohols | 0% | 0% |

The results from example IV demonstrate that pretreating the invention catalyst in a manner similar to the pretreatment given the control catalysts leads to catalysts of poor activity. The selectivity of the catalysts is not noticeably affected by this treatment, however. Thus, the catalyst preparation described herein leads to catalysts with activities superior to the activity of catalysts prepared by conventional methods. It is obvious that many variations may be made in the present invention without departing from the spirit of the scope thereof.

We claim:

1. A process for producing hydrocarbons comprising contacting synthesis gas under converting conditions of temperature and pressure with a catalyst comprising a support material chosen from the group consisting of silicon dioxide, aluminum oxide, activated carbon, magnesium oxide, titania and mixtures thereof impregnated with solvated metal atoms chosen from the group consisting of iron and cobalt with a metal content of said finished catalyst ranging from an amount sufficient to be catalytically effective up to about 5 weight percent, based on the weight of said catalyst, wherein said solvated metal atoms are impregnated on said support material by vaporizing the metal in the presence of a solvent, forming a vaporous solvent/metal mixture, cooling said mixture to very low temperatures to form a cocondensed solvent/metal solid mixture, warming said solid mixture to form a metal in solvent slurry, contacting said metal in solvent slurry with said support material and removing said solvent.

2. A process according to claim 1 where said solvent is chosen from pentane, hexane, toluene, tetrahydrofuran and dioxane, and mixtures thereof.

3. A process according to claim 2 where said solvent is toluene.

4. A process according to claim 1 where the metal content ranges from about 2 to about 5 weight percent, based on the weight of said catalyst.

5. A process according to claim 1 where said converting condition of temperature ranges from about 150° C. to about 450° C., said pressure ranges from about atmospheric to about 1000 atmospheres, where said process operates at a H$_2$/CO mol ratio ranging from about 0.2 to about 6, and a space velocity ranging from about 500 to about 50,000 vol/vol/hr.

6. A process according to claim 1 where said converting condition of temperature ranges from about 150° C. to about 350° C., said pressure ranges from about atmospheric to about 30 atmospheres, where said process operates at a H$_2$/CO mol ratio ranging from about 1 to about 2.5, and a space velocity ranging from about 500 to about 2000 vol/vol/hr.

7. A process for producing hydrocarbons comprising contacting synthesis gas under converting conditions of temperature and pressure with a catalyst composition comprising a support material of silicon dioxide impregnated with solvated metal atoms chosen from the group consisting of iron and cobalt with the metal content of said finished catalyst ranging from an amount sufficient to be catalytically effective up to about 5 weight percent, based on the weight of said catalyst, wherein said solvated metal atoms are impregnated on said support material by vaporizing the metal in the presence of a solvent, forming a vaporous solvent/metal mixture, cooling said mixture to very low temperatures to form a cocondensed solvent/metal solid mixture, warming said solid mixture to form a metal in solvent slurry, contacting said metal in solvent slurry with said support material and removing said solvent.

8. A process according to claim 7 where said solvent is chosen from pentane, hexane, toluene, tetrahydrofuran and dioxane, and mixtures thereof.

9. A process according to claim 8 where said solvent is toluene.

10. A process according to claim 7 where the metal content ranges from about 2 to about 5 weight percent, based on the weight of said catalyst.

11. A process according to claim 7 where said converting condition of temperature ranges from about 150° C. to about 450° C., said pressure ranges from about atmospheric to about 1000 atmospheres, where said process operates at a H$_2$/CO mol ratio ranging from about 0.2 to about 6, and a space velocity ranging from about 500 to about 50,000 vol/vol/hr.

12. A process according to claim 7 where said temperature ranges from about 150° C. to about 350 C., said pressure ranges from about atmospheric to about 30 atmospheres, where said process operates at a H$_2$/CO mol ratio ranging from about 1 to about 2.5, and a space velocity ranging from about 500 to about 2000 vol/vol/hr.

* * * * *